United States Patent [19]
Levy

[11] Patent Number: 5,116,227
[45] Date of Patent: May 26, 1992

[54] PROCESS FOR CLEANING AND ENLARGING PASSAGES

[75] Inventor: Guy Levy, Tustin, Calif.

[73] Assignee: Endo Technic Corporation, San Clemente, Calif.

[21] Appl. No.: 663,425

[22] Filed: Mar. 1, 1991

[51] Int. Cl.⁵ .............. A61C 15/00; A61C 5/00; A61C 5/02
[52] U.S. Cl. ................. 433/216; 433/215; 433/224; 606/7
[58] Field of Search .......... 433/216, 224, 229; 606/4, 7; 604/22

[56] References Cited

U.S. PATENT DOCUMENTS

| | | | |
|---|---|---|---|
| 4,273,535 | 6/1981 | Yamamoto et al. | 433/216 |
| 4,503,853 | 3/1985 | Ota et al. | 606/7 |
| 4,583,539 | 4/1986 | Karlin et al. | 606/4 |
| 4,784,135 | 11/1988 | Blum et al. | 606/7 |
| 4,791,927 | 12/1988 | Menger | 606/10 |
| 4,832,023 | 5/1989 | Murphy-Chutorian | 606/7 |
| 4,848,336 | 7/1989 | Fox et al. | 606/7 |
| 4,850,872 | 7/1989 | Goldman et al. | 433/215 |
| 4,940,411 | 7/1990 | Vassiliadis et al. | 433/215 |

Primary Examiner—Gene Mancene
Assistant Examiner—Cindy A. Cherichetti
Attorney, Agent, or Firm—Spensley Horn Jubas & Lubitz

[57] ABSTRACT

A process for cleaning and/or shaping passages, comprising providing an optical fiber having a diameter sufficiently small to be introduced into the passage and having a free end provided with a radiation focussing element; introducing the free end of the fiber into the passage so that the focal point defined by the radiation focussing element is located adjacent the region to be cleaned or shaped; providing a liquid in the passage at the location of the focal point of the radiation focussing element; and supplying pulses of laser radiation to the fiber so that the radiation exits the fiber via the free end to provoke a cavitation of vapor at the interior of the irrigating liquid.

15 Claims, 1 Drawing Sheet

PROCESS FOR CLEANING AND ENLARGING PASSAGES

BACKGROUND OF THE INVENTION

The present invention relates to the cleaning and/or enlargement, or shaping, of passages in bodies made of a variety of materials. The invention is particularly applicable, but not limited, to passages in mineral or organic structures encountered in the fields of dentistry and medicine.

The state of the art with respect to dental applications will be discussed, solely by way of example.

The second step in the usual endodontic procedure involves cleaning and widening of the tooth canal. Cleaning involves removal of soft tissue, i.e., pulp and nerve tissue, while widening or enlargement of the canal requires removal of dentin material forming the canal wall. Conventionally, these operations are performed with the aid of a series of files having progressively increasing diameters and working in a moist medium. This work is performed most commonly by manual operation of the files and while introducing and irrigating fluid into the canal with the aid of a syringe. Such techniques are demanding inasmuch as they require very precise longitudinal movements, causing the practitioner to experience fatigue, which is physical as well as in the form of stress, since it is virtually impossible to control the action of such a file in a perfect manner.

Recently, automated techniques have made possible simultaneous cleaning and enlargement of tooth canals, with the aid of sonic or ultrasonic energy which, by vibrating a dental file, permits: enlargement due to high frequency movements induced in the file; and cleaning due to turbulence created in the irrigating fluid contained in the canal.

These automated techniques, however, have their own inherent drawbacks in that, for example, the vibrations induced in the files are on occasion disagreeable or poorly controlled by the practitioner. In particular, these vibrations require a very precise control during manipulation, which renders the use of these techniques very demanding.

SUMMARY OF THE INVENTION

It is an object of the present invention to provide a novel process and method which alleviates many of the inconveniences associated with prior art techniques for the enlargement and cleaning of a passage. A more specific object of the invention is to allow such operations to be carried out under more precise control by the practitioner, without imposing undue demands on the practitioner.

Yet another object of the invention is to reduce the time required to perform such enlargement and cleaning procedures.

The above and other objects are achieved, according to the present invention, by a process for cleaning and/or shaping passages, comprising providing an optical fiber having a diameter sufficiently small to be introduced into the passage and having a free end provided with a radiation focussing element; introducing the free end of the fiber into the passage so that the focal point defined by the radiation focussing element is located adjacent the region to be cleaned or shaped; providing a liquid in the passage at the location of the focal point of the radiation focussing element; and supplying pulses of laser radiation to the fiber so that the radiation exits the fiber via the free end to transform a portion of the liquid into vapor and provoke a cavitation of the vapor at the interior of the irrigating liquid.

Various studies have demonstrated the possibility of creating a cavitation of a vapor with the aid of a laser. For example, in 1979, D. C. Emmony and, more recently, in 1987, F. Giovanneschi-Testud, have demonstrated the existence of a cavitation of vapor and water, induced by a Nd YAG laser.

According to the present invention, the cleaning and enlargement of passages in physiologic tissue, such as tooth canals, containing or composed of mineral and/or organic substances, is achieved by provoking a cavitation of vapor within a liquid introduced into, or present in, the canal, with the aid of a laser beam or laser radiation delivered and focussed by means of an optical fiber. Implosion of bubbles of gas, created by the cavitation of vapor at the interior of the liquid contained in the canal, causes an erosion of the walls of the canal, and, as a result, a cleaning and enlargement thereof.

The cleaning and enlargement method according to the present invention offers the following significant advantages: the absence of vibration; ease of utilization; a time-action relationship which can be fully predetermined; the possibility of controlling the zone of action as a function of the focal length presented by the optical fiber; and a control of the parietal action on the canal as a function of the number of laser radiation pulses.

The mechanism described above may also advantageously be used for disintegrating plaque or atheromas in blood vessels or similar deposits in other body passages, such as urinary canals.

DESCRIPTION OF THE PREFERRED EMBODIMENTS

The process according to the present invention is particularly remarkable in that cleaning and enlargement of canals, or other passages, particularly those formed by mineral and organic substances, can be effected by provoking a cavitation of vapor within a liquid present or introduced in the passage by the delivery of energy, in the form of laser radiation, to the interior of the canal, and focussing the radiation, with the aid of an optical fiber.

In an advantageous manner, according to the application of the invention to the cleaning and enlargement of tooth canals, the irrigating fluid is water, which may be demineralized or mineralized, and in a particularly advantageous manner, a type of irrigation solution most frequently employed during the performance of dental procedures in a canal, i.e., water containing 0.5-2.5% NaClO.

The radiation absorption minimum of this liquid corresponds to a wavelength of between 0.530 and 1.06 $\mu$. This wavelength corresponds to the characteristic wavelengths of Nd-YAG lasers, whose radiation wavelength can be regulated to have a value of 0.530, 0.750, or 1.06 $\mu$. Use can also be made of ruby lasers whose wavelength is 0.694 $\mu$.

To obtain a cavitation of vapor in this liquid, the liquid being transparent to these wavelengths, it is sufficient to focus the laser radiation to create a point at which there is a high light intensity.

In an advantageous manner, this cavitation of vapor is created by means of a beam or radiation from a YAG laser which permits the energy to be transported with the aid of an optical fiber that is sufficiently thin to be introduced into a tooth canal (0.30 mm) in a manner to focus, or concentrate, the radiation at the free end of the fiber.

The free end of the fiber can be given the form of a lens having a focal length selected to permit displacement of the zone of cavitation by a desired distance from the free end of the fiber, which assures the creation of an enlargement action at various distances from the free end of the fiber.

Thus, the focal length imparted to this lens at the free end of the fiber permits a focussing of the radiation at a location more or less spaced from the free end of the fiber. Focussing of the laser beam creates, at the focal point, the generation of a bubble which then implodes while provoking an erosion of the adjacent canal wall.

Figure 1:
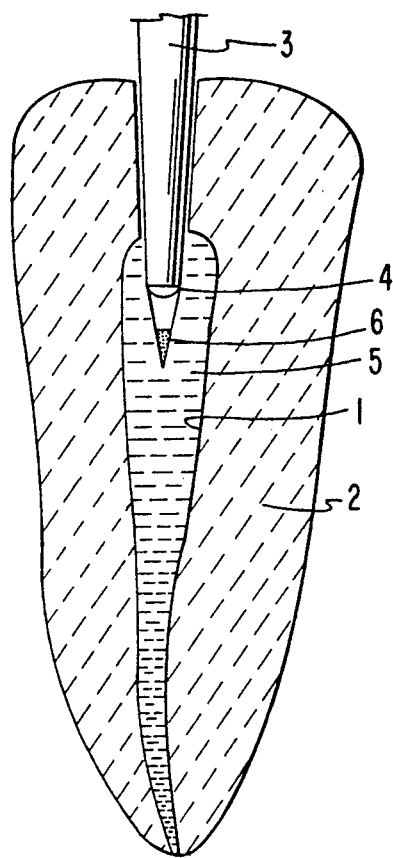
FIGS. 1 and 2 are cross-sectional views illustrating the practice of the present invention in a tooth canal.
Figure 2:
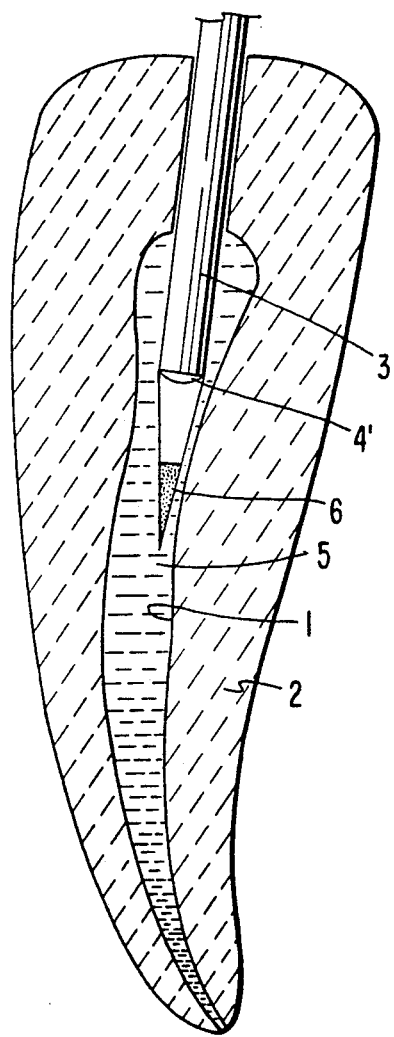

FIGS. 1 and 2 illustrate a tooth 2 having a dental or radical canal 1. After canal 1 is opened via the crown of tooth 2, an optical fiber 3 having its free end shaped in the form of a converging lens 4, 4' is introduced into canal 1. Lens 4 of the embodiment shown in FIG. 1 has a shorter focal length than does lens 4' of the embodiment shown in FIG. 2.

Laser radiation in the form of pulses conducted via fiber 3 is focussed to create a zone of cavitation 6. Focussing of the radiation beam creates, at the focal point of lens 4 or 4', a bubble which, upon termination of the laser radiation pulse, implodes while provoking an erosion of the adjacent wall of canal 1. Depending on the focal length of lens 4 or 4', the cavitation will be provoked at a greater or lesser distance from lens 4 or 4'.

Cleaning of canal 1 is achieved by shock waves resulting from the laser radiation pulses, producing vapor implosions which detach debris or tissue from the wall of canal 1.

The size of the cavitation bubbles decreases as the focal length increases, a preferred focal length being between 1 and 10 mm.

The length, or duration of each laser radiation pulse will be selected in dependence on the diameters of fiber 3 and canal 1 and vary over a wide range. For certain applications, it has been found that a pulse duration of 10-20 ns is suitable. However, longer pulse lengths can be employed, particularly for larger fiber and/or canal diameters.

The energy of each radiation pulse is also selected on the basis of fiber and canal diameters. While the energy per pulse can be of the order of 0.5 to 5 mJ, higher energy levels can be employed, particularly for larger fiber and/or canal diameters.

A shock wave produced by each radiation pulse propagates and terminates within a period of 50 nanoseconds and a pulse repetition rate of between 1 and 100 Hz can be suitably employed.

There will now be described an example of the practice of the present invention, which example is not intended to be limitative of the scope of the invention.

During a first period, an access passage is prepared, i.e., the tooth canal or radical canal 1 is enlarged to a diameter of 0.25 mm by means of conventional instruments, such as files, along the entire length of the root canal of tooth 2, to a point about 1 mm from the apex. Penetration by the files may be monitored by radiologic means. This corresponds to the first step of an endodontic procedure which is here carried out in a conventional manner.

Then, irrigating liquid 5 is introduced into canal 1, for example with the aid of a syringe, and the free end of fiber 3 is introduced into canal 1, the other end of fiber 3 being coupled to a laser. In addition, liquid 5 can be introduced around fiber 3 during and after insertion of the latter to ensure that canal 1 is filled with the liquid continuously during the cleaning and enlargement, or shaping, process.

For a straight canal, an optical fiber having a diameter of 0.30 mm with a lens 4 having a short focal length, as shown in FIG. 1, permits widening of the upper third of canal 1, by utilizing a sequence of laser radiation shots which can have the following parameters: a pulse duration of 10 ns to several milliseconds; and energy per pulse of 2 mJ to 1 J; and a repetition rate of 30-100 Hz.

This operation is continued until the diameter of canal 1 is increased to 0.80 mm.

Then, use can advantageously be made of a second optical fiber having a diameter of 0.30 mm with a lens 4' having a longer focal length as shown in FIG. 2, to the apical two thirds of the root. The progress of the shaping can be monitored after each sequence of laser radiations shots, or pulses.

For the cleaning and shaping of curved tooth canals, the utilization of only an optical fiber having a lens with a short focal length is recommended.

It will be noted that optical fiber 3 shown in FIG. 1 tapers towards its outlet end. Proper selection of the degree of taper helps to concentrate the laser radiation at the free end of fiber 3.

While the description presented above has been with reference to the treatment of root canals, it should be appreciated that the same technique can be employed in a wide variety of situations to clean and enlarge passages in materials such as ceramics, plastics and metals.

The technique according to the further invention can further be usefully applied to the difficult task of removing posts which had previously been implanted in the mouth to support artificial filling to restore a tooth. Known techniques for performing this operation are difficult to implement and relatively dangerous because they present the possibility of perforating the tooth root. It has been proposed to loosen such posts by means of ultrasonic vibrations, but to date this has only been partially successful.

According to the invention, the free end of an optical fiber is brought into contact with the post near the point where the post enters the root and the associated laser is activated at an energy level of 200 to 300 mJ, with a repetition rate of 50 hertz and a pulse duration of 0.4 to 1 millisecond, the region surrounding the post having previously been filled with a liquid. Due to the vibrations produced by the pulses and the cavitation effects resulting from the interaction of the laser radiation pulses with the liquid, the post becomes loosened and can then be removed without exposing the root structure to any damage.

Moreover, the technique can also be employed in the medical field for cleaning vessels, such as blood vessels, for example to remove plaque deposits, or atheromas. For such applications, the fiber is introduced to the location to be cleaned and the parameters of the radiation pulses are selected on the basis of the nature of the vessel and its diameter.

Figure 3:
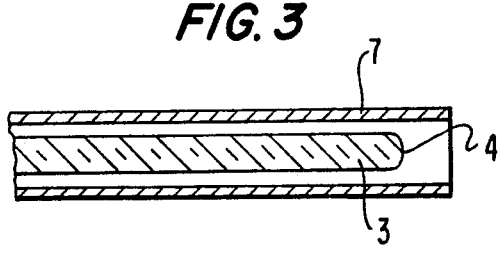
FIG. 3 is a cross-sectional view illustrating apparatus for practicing the invention in a body passage.

FIG. 3 illustrates a simple device which can be employed for this purpose, which device essentially includes a hollow catheter 7, which may be made of plastic, is inserted into a blood vessel so that the distal end of catheter 2 is placed a short distance, possibly 1 to 2 millimeters, from the deposit. Optical fibre 3 is disposed within tube 7 and its lens 4 may be located in line with the distal end of catheter 7 or slightly retracted therefrom. Fiber 3 may have a diameter of the order of 150 microns.

The interior of tube 7 is flooded with a suitable physiologic solution which is supplied so as to exit from the distal end of catheter 7 while under a slight pressure. This creates a favorable environment for the cavitation action. Then the laser which is connected to the proximal end of fiber 3 is activated so that laser radiation pulses are introduced into the liquid at a focal point beyond lens 4. The energy of each laser radiation pulse can be in the range of 5-200 mJ, the preferred value being higher for larger vessel diameters. Here again, a pulse repetition rate of 32 to 100 hertz and a pulse duration of 10ns to several ms may be employed.

During or subsequent to application of a series of such pulses, the region being treated can be subjected to suction in order to remove disintegrated material.

This technique offers advantages over previously proposed techniques utilizing laser energy, which techniques require that the distal end of the fiber be in contact with the deposit, since it is proven difficult to place the distal end of the fiber in contact with the deposit while being out of contact with the wall of the blood vessel. The technique according to the present invention eliminates the need for the optical fiber to contact the deposit and avoids heating of the blood vessel wall. Since fiber 3 can remain substantially completely within catheter 7, the fiber itself is prevented from contacting the blood vessel wall.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A process for cleaning and/or shaping a passage, comprising: providing an optical fiber having a diameter sufficiently small to be introduced into the passage and having a free end provided with a radiation focussing element; introducing the free end of the fiber into the passage so that the focal point defined by the radiation focussing element is located adjacent the region to be cleaned or shaped; providing a liquid in the passage at the location of the focal point of the radiation focussing element; and supplying pulses of laser radiation to the fiber so that the radiation exits the fiber via the free end to transform a portion of the liquid into vapor and provoke a cavitation of the vapor at the interior of the liquid.

2. A process according to claim 1 wherein the irrigating liquid is constituted by demineralized water.

3. A process according to claim 1 wherein the irrigating liquid is constituted by mineralized water.

4. A process according to claim 1 wherein the irrigating liquid is constituted by an aqueous solution of sodium hypochlorite.

5. A process according to claim 1 wherein the laser radiation is produced by a YAG laser.

6. A process according to claim 5 wherein the laser a Nd-HAG laser producing radiation of a wavelength of 0.530, 0.750 or 1.06 $\mu$.

7. A process according to claim 1 wherein the laser radiation is produced by a ruby laser at a radiation wavelength of 0.694 $\mu$.

8. A process according to claim 1 further comprising providing a plurality of optical fibers whose free ends are provided with radiation focussing elements having respectively different focal lengths, utilizing one of said fibers whose radiation focussing element has a short focal length on the proximal portion of the passage, and utilizing a second one of said optical fibers whose radiation focussing element has a long focal length for the distal portion of the passage.

9. A process according to claim 1 for cleaning and/or shaping a curved tooth canal wherein the radiation focussing element of the optical fiber has a short focal length.

10. A process according to claim 1 wherein the laser radiation is in the form of a series of pulses having a pulse duration of 10 ns to several ms, an energy per pulse of 2m J to 1 J, and a repetition rate of 30 to 100 Hz.

11. A process as defined in claim 1 wherein the passage is a canal in a tooth.

12. A process as defined in claim 1 wherein the passage is in a vessel of physiological material.

13. A process as defined in claim 12 wherein the vessel is a blood vessel containing a deposit, and said method further comprises introducing a tube having a distal end into the vessel so that the distal end of the tube is spaced a small distance from the deposit, and wherein said step of introducing the free end of the fiber is carried out by introducing the free end of the fiber into the tube so that the radiation focussing element of the fiber is located in proximity to the distal end of the tube.

14. A process as defined in claim 1 wherein the passage is constituted by the interior of a tube made of ceramic, plastic, or metal.

15. A process according to claim 1 wherein said step of supplying pulses of laser radiation is carried out so that the radiation focusing element focuses the laser radiation which exits from the fiber within the liquid.

* * * * *